United States Patent [19]

Leung et al.

[11] Patent Number: 5,200,177
[45] Date of Patent: Apr. 6, 1993

[54] TREATMENT OF ATOPIC DISORDERS WITH GAMMA-INTERFERON

[75] Inventors: Donald Y. M. Leung, Englewood, Colo.; Raif S. Geha, Belmont, Mass.

[73] Assignee: The Children's Medical Center Corporation, Boston, Mass.

[21] Appl. No.: 912,564

[22] Filed: Jul. 13, 1992

Related U.S. Application Data

[63] Continuation of Ser. No. 444,763, Dec. 1, 1989, abandoned.

[51] Int. Cl.$^5$ .............................................. A61K 37/66
[52] U.S. Cl. .................................. 424/85.5; 514/826; 514/861
[58] Field of Search ................ 424/85.5; 514/826, 861

[56] References Cited

FOREIGN PATENT DOCUMENTS

WO83/01198 of 1983 PCT Int'l Appl. .
WO87/01288 of 1987 PCT Int'l Appl. .
WO87/07842 of 1987 PCT Int'l Appl. .
WO88/09674 of 1988 PCT Int'l Appl. .

OTHER PUBLICATIONS

Goodman and Gillman's: The Pharmacological Basis of Therapeutics, 8th Ed., p. 632, (1990).
McFadden Harrison's Principles of Internal Medicine, 12th Edition, pp. 1047–1053 (1991).
Stedman's Medical Dictionary, 24th Edition p. 443.
H. C. Maguire et al., *Int. Arch. Allergy Appl. Immunol.*, 88:345 347 (1989).
J. M. Parkin et al., *Br. Med. Journal*, 294:2285-1186 (1987).
M. Boduniewicz et al., *J. Allergy Clin. Immunol.*, 83:196 (1989) (Abstract).
D. Y. M. Leung et al., *Clin. Res.*, 37(2):239A (Apr. 1989) (Abstract).

*Primary Examiner*—Merrell C. Cashion, Jr.
*Assistant Examiner*—Choon P. Koh
*Attorney, Agent, or Firm*—Hamilton, Brook, Smith & Reynolds

[57] ABSTRACT

A method of treating patients having chronic, severe allergic disorders, such as atopic dermatitis or steroid-dependent asthma, with gamma interferon is disclosed. The method involves treating patients afflicated with atopic dermatitis or steroid-dependent asthma with effective dosages of gamma interferon, which reduces the clinical severity of their disease.

9 Claims, 3 Drawing Sheets

TREATMENT OF ATOPIC DISORDERS WITH GAMMA-INTERFERON

This is a continuation of co-pending application Ser. No. 07/444,763 filed on Dec. 1, 1989, now abandoned.

BACKGROUND

Atopic dermatitis (AD) is a common inflammatory skin disease characterized by severe pruritus, a chronically relapsing course with frequent periods of exacerbation, a distinctive clinical morphology and distribution of skin lesions. Chronic AD may result in significant morbidity including hospitalization for control of skin disease and infection, school days lost, psychological trauma from physical disfigurement, occupational disability and the need for long term use of medications. The management of AD has been less than satisfactory and is directed toward symptomatic relief of symptoms or complications of this illness. J. M. Hanafin, *J. Amer. Acad. Dermatol.*, 6: 1-13 (1982); D. Y. M. Leung et al., In: *Dermatology and General Medicine*, Fitzpatrick et al., (eds.), pp. 1385-1408, McGraw-Hill, Inc., New York (1986).

Although the primary cause of AD is unknown, substantial evidence suggests that excessive production of IgE directed to both food and inhalant allergens contributes to the pathogenesis of this disease. H. A. Sampson, *J. Allergy Clin. Immunol.*, 81: 635-645 (1988); L. Tuft et al., *J. Allergy*, 23: 528-540 (1952). Recent studies have demonstrated that interferon gamma (IFN-$\gamma$) suppresses in vivo and in vitro IgE synthesis in experimental animals, as well as IL-4 induced IgE synthesis in vitro by human peripheral blood mononuclear cells (PBMC). G. M. Snapper et al., *Science*, 236: 944-946 (1987); F. P. Heinzel et al., *J. Exp. Med.*, 169: 59-72 (1989); R. L. Coffman et al., *J. Immunol.*, 136: 949-954 (1986); F. D. Finkleman et al., *J. Immunol.*, 140: 1022-1027 (1988). Patients with AD have been reported to have a number of T cell abnormalities including impaired supressor/cytotoxic T cell function and decreased capacity to produce IFN-$\gamma$ in response to a number of stimuli. D. Y. M. Leung et al., *J. Immunol.*, 130: 1678-1682 (1983); D. Y. M. Leung et al., *Clin. Rev. Allergy*, 4: 67-86 (1986); U. Reinhold et al., *Int. Arch. Allergy Appl. Immunol.*, 87: 120-126 (1988).

An effective treatment for chronic allergy-related disorders such as AD is needed.

SUMMARY OF THE INVENTION

The present invention relates to a method for treating chronic atopic dermatitis (AD) using IFN-$\gamma$. In the present method, IFN-$\gamma$ is administered in vivo to the patient in an amount sufficient to produce an improvement in the clinical symptoms of the disorder. The method is also effective for treating severe forms of asthma, such as steroid-dependent asthma.

IFN-$\gamma$ can be used as an adjunct in the treatment of allergic disorders. For example, IFN-$\gamma$ treatment can be combined with treatment with one or more anti-allergic drugs, bronchodilators, cytokines or immunomodulators.

IFN-$\gamma$, used alone or as an adjunct, is a particularly effective drug for treating chronic, severe AD and steroid-dependent asthma.

DETAILED DESCRIPTION OF THE INVENTION

Figure 1:
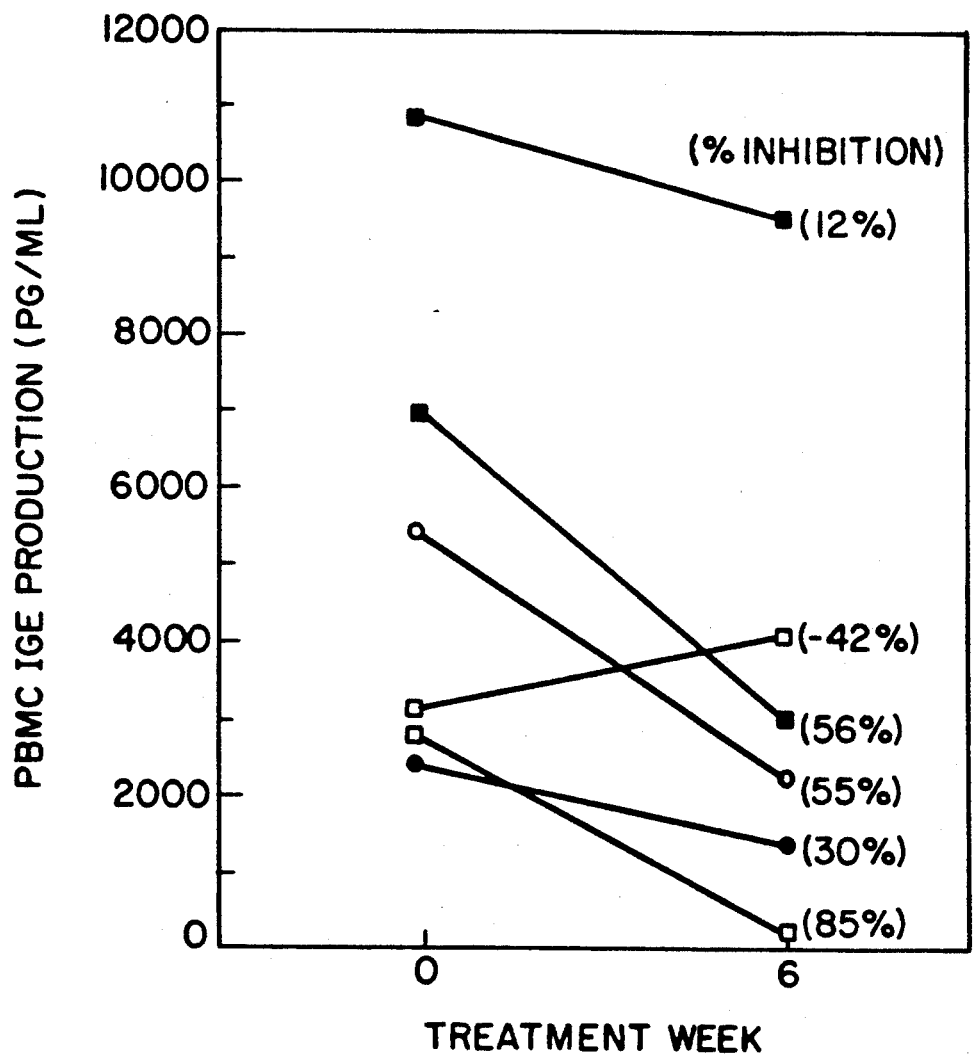
FIG. 1 is a graph showing the reduction of spontaneous IgE synthesis by peripheral blood mononuclear cells from atopic dermatitis patients over 6 weeks of daily rIFN-$\gamma$ treatment (0.05 mg/M$^2$).

In the present method, patients afflicted with a chronic, severe allergic disorder, particularly atopic dermatitis (AD) or steroid-dependent asthma, are treated with IFN-$\gamma$. As used herein, the term "atopic" disorders or diseases refers to Type I allergic reactions generally caused by allergens such as, e.g., food, dander, or insect venom, which are associated with increased serum levels of IgE.

The present method involves treating individuals afflicted with chronic severe, AD by administering to the individual an amount of IFN-$\gamma$ sufficient to reduce, ameliorate or eliminate the clinical symptoms of the disease. AD is a chronic or intrinsic form of dermatitis which can be caused by a type I allergic reaction. There is no known curative therapy for AD. AD is related to increased production of IgE which is triggered by allergens, unlike acute forms of dermatitis (e.g., contact dermatitis or psoriasis), which are not IgE-mediated. Contact dermatitis, and psoriasis are different from AD, in that they are not allergic disorders and are immunologically distinct in that they are T-cell mediated disorders.

In the present method, IFN-$\gamma$ can be administered orally, by subcutaneous or other injection, intravenously, parenterally, transdermally or via an implanted reservoir or a sustained-release drug delivery device containing IFN-$\gamma$. The form in which the drug will be administered (e.g., powder, capsule, solution, emulsion) will depend upon the route by which it is administered.

The quantity of IFN-$\gamma$ to be administered will depend in part on consideration of the individual's size, the severity of the symptoms to be treated and the result sought. In general, quantities of IFN-$\gamma$ sufficient to reduce, ameliorate or eliminate the clinical symptoms of AD will be administered. For example, dosage levels of from about 0.01 mg/M$^2$ to about 0.1 mg/M$^2$ (M$^2$ refers to square meters of total skin surface of the individual) per day, given in one dose or a number of smaller doses, will be adequate in most individuals to produce the desired effect. Subcutaneous administration is a preferred route, since it is as effective and can be performed by the patient at home, and therefore does not require hospitalization.

In general, the IFN-$\gamma$ or composition containing IFN-$\gamma$ is administered to an individual periodically as necessary to improve symptoms of the disease being treated. The length of time during which the drug is administered and the dosage will depend upon, inter alia, the type and severity of the symptoms and the physical condition of the individual being treated.

IFN-γ from any source can be used in the present method, including IFN-γ isolated from naturally-occurring sources and recombinant IFN-γ (rIFN-γ). As used herein, IFN-γ includes all proteins, peptides and polypeptides which are characterized by the biological activity of IFN-γ, for example, natural and recombinant IFN-γ or derivatives thereof. These include IFN-γ-like compounds from a variety of sources such as natural IFN-γ, recombinant IFN-γ and synthetic IFN-γ or combinations thereof. For example, IFN-γ useful in the present method includes natural IFN-γ produced in vitro by established or transformed cell lines and natural IFN-γ produced in vitro by a variety of cells in response to interferon inducers. IFN-γ useful in the present method also includes IFN-γ produced by cloning and expression of various host/vector systems using recombinant DNA technology. Recombinant IFN-γ is particularly useful because it is readily available and cost-effective.

In another embodiment of the present method, IFN-γ or rIFN-γ can be used in adjunctive treatment combined with other drugs for reducing, ameliorating or eliminating the symptoms of AD. In this method, IFN-γ is administered in conjunction with other drugs, including anti-allergy drugs (e.g., antihistamines), topical or systemic steroids, bronchodilators (e.g., theophylline), beta-adrenergic drugs, immunomodulators (e.g., cyclosporin, methotrexate) or cytokines (e.g., TNF, TGF-β, IFN-α, IL-2).

The composition to be administered can optionally include, in addition to IFN-γ or rIFN-γ, other components. The components included in a particular composition are determined primarily by the manner in which the composition is to be administered. In the case of adjunctive treatment with IFN-γ, IFN-γ is administered either concurrently with or in close temporal proximity to one or more drugs. For example, a composition to be administered in liquid form, by injection or other method, can include the IFN-γ or rIFN-γ, an adjunctive drug, if appropriate, and optionally, a physiologically compatible solvent (e.g., PBS, isotonic saline, water, dextrose), emulsifying agents or coloring agents. A composition to be administered orally can include in addition to INF-γ, a filler (e.g., lactose) a binder (e.g., carboxymethyl cellulose, gelatin) an adjuvant, flavoring agent, coloring agent or coating material.

The present method is useful to treat patients whose AD symptoms do not respond to conventional treatments, such as emollients, potent topical or systemic steroids and anti-histamines. The present method is also useful to treat chronic, severe steriod-dependent asthma, by in vivo administration of IFN-γ. Steroid-dependent asthma is a severe form of IgE-mediated extrinsic (i.e., allergic) asthma. This type of asthma requires the frequent or constant use of systemic steroids by the afflicted person to control the asthma symptoms. In this embodiment, IFN-γ is administered in an amount sufficient to reduce, ameliorate or eliminate the symptoms of steroid-dependent asthma.

The invention is further illustrated by the following Exemplification.

EXEMPLIFICATION

Materials and Methods

Study Design

Recombinant IFN-γ (Genentech, South San Francisco, Calif.; specific activity approximately $2 \times 10^7$ U per milligram of protein [referenced to the National Institutes of Health interferon standard Gg23901530]) was supplied as an endotoxin-free lyophil, and reconstituted in distilled water. The study protocol consisted of two parts.

Part I was designed primarily to determine the maximum dose of rIFN-γ that would be well tolerated in this patient population. In this part, 14 patients were treated with rIFN-γ at three successive dose levels (DL): DL1 was 0.01 mg/$M^2$, DL2 was 0.05 mg/$M^2$, DL3 was 0.1 mg/$M^2$. Each dose was administered once daily by subcutaneous injection for five days with two days off between each DL. Clinical condition, routine laboratory studies, and IgE production were evaluated at the time of screening, on days 1 and 5 of each DL, then 3 days off treatment.

In part II, 8 patients received rIFN-γ at DL2 (0.05 mg/$M^2$) daily for 6 weeks. Clinical condition, routine laboratory studies, and IgE production were evaluated at the time of screening and on days 7, 21, and 42. Nine patients, one from part I and 8 from part II, were placed on maintenance therapy with rIFN-γ for the purpose of gathering long term tolerance data and to examine effects of long term rIFN-γ administration on serum IgE levels.

Patients and Assessment of Their Disease Activity

Twenty-two patients with chronic, severe AD were entered into a phase 1/pilot study to determine the tolerance and efficacy of rIFN-γ in this patient population. Eligibility for this study required that the patient be 5 years of age or older, and have had a diagnosis of active chronic AD of at least 3 months duration. Diagnostic criteria for AD were those used by Hanifin and Rajka. Hanifin and Rajka, *Acta Dermatol. Venereol.,* 92(supp.): 44–47 (1980). In addition, all patients had to have an elevated serum IgE level (greater than 2 standard deviations above the mean for age) and a personal or family history of allergic respiratory disease or AD. Patients had to have a clinical severity score of 6 or greater (including a score of 2 or more for both erythema and pruritus) within 1 week prior to entry. The total clinical severity score (0–15) was defined as the sum of the individual scores, graded as 0 (none), 1 (mild), 2 (moderate) and 3 (severe), for each of five parameters: pruritus, erythma, edema/population, excoriation and scaling/dryness.

The extent of skin disease was estimated using the rule of nines. Barkin and Burrington, *In: Current Pediatric Diagnosis and Treatment,* C. H. Kempe et al., eds., p. 207, Appleton and Lange, Norwalk (1987). All patients had to have involvement of at least 20% of their body surface area.

The clinical and laboratory features of the patients entered into this protocol are summarized in Table I.

TABLE I

| Characteristics of AD Patients Entered into Open Label Study of Gamma Interferon Treatment | | |
|---|---|---|
| Characteristic | Part I | Part II |
| Sex (M/F) | 9/5 | 4/4 |
| Median Age (Yrs) | 33 | 25 |
| Serum IgE (IU/ml) | 10,500(680–59,100) | 6420(573–65,700) |
| Duration of AD(Yrs) | 28(3–47) | 18(13–51) |
| % Body Involvement | 72(40–100) | 81(27–100) |
| Total Clinical Severity | 13(9–15) | 14(9–15) |

All patients had a history of chronic severe AD which had not responded well to previous treatment with standard therapy including the use of emollients, potent topical steroids, and anti-histamines. Most patients had required past hospitalizations or systemic steroids for control of their skin disease.

Quantitation of Serum Immunoglobulin Levels

Serum IgE levels were measured by a commercially available solid phase, two-site immunoenzymetric assay (Hybritech Inc; San Diego, Calif.). Serum IgG, IgM, and IgA were measured by the Mancini Single Radial Immunodiffusion technique (Kallestad Labs; Austin, Tex.).

Assessment of Spontaneous IgE Production by PBMC

The method used for assessment of spontaneous IgE production by atopic peripheral blood mononuclear cells (PBMC) is described in detail in: Saryan et al., J. Clin. Invest., 71: 556–564 (1983); and Young et al., Eur. J. Immunol., 16: 985–991 (1986). Briefly, blood samples were collected in preservative-free heparin and PBMC were separated by centrifugation on Ficoll-Hypaque. PBMC were suspended in RPMI-1640 (M.A. Bioproducts, Walkersville, Md.) supplemented with penicillin (100 U/ml), streptomycin (50 g/ml), and 10% heat-inactivated FBS (Hyclone, Sterile Systems, Inc., Logan, Utah) at a cell concentration of 1.5 million cells per ml. These PBMC were cultured at 37° C. in a 5% $CO_2$ humidified atmosphere. After 10 days, the culture supernatants were harvested and assessed by solid phase radioimmunoassay (RIA) for their IgE content as previously described. Saryan et al., ibid; and Young et al., ibid. The lower limit of sensitivity of this assay is 150 pg/ml. The sensitivity and specificity of this assay for IgE was validated in a recent multicenter collaborative assessment of assays used for measurement of small quantities of IgE in cell culture supernatants. Helm et al., J. Allergy Clin. Immunol., 77: 880–890 (1986). IgE associated with the cell pellet on day 0 of culture and day 10 of culture was determined by acid treatment of the cell pellet as previously described by Turner et al. Turner et al., Clin. Exp. Immunol., 51: 387–394 (1983). De novo or net IgE synthesis was calculated by subtracting the values for IgE obtained in day 0 acid treatment cell pellets, i.e., in vivo performed IgE, from IgE values of day 10 culture supernatants plus day 10 cell pellets.

Statistical Analysis

For part I, changes between day 1 and day 5 of each DL for serum IgE, spontaneous IgE synthesis and total clinical severity were analyzed using a two-sided sign test or Wilcoxon signed-rank test. Changes within each DL for each patients were also similarly compared to baseline changes between screening to DL1, day 1. In part II, the changes over time for each patient in serum IgE, spontaneous IgE synthesis and total clinical severity were statistically assessed using the two-sided sign test or Wilcoxon signed-rank test.

RESULTS

Fourteen AD patients entered into part I of the protocol. All 14 patients completed DL1 without any adverse reactions. On DL2, three of the 14 patients had transient headaches or myalgias (4% of doses). One patient dropped out of the study at DL2 for personal reasons. On DL3, nine of the 13 remaining patients experienced transient headache, malaise, fever/chills, myalgia, nausea (25% of doses). The only significant lab abnormality noted was a dose dependent reversible decrease in neutrophil count at each DL. No patient, however, developed absolute neutropenia (<1000 neutrophils per cu mm) during the study.

Two parameters of IgE production were measured serially during this study: first, serum IgE levels; and second, spontaneous IgE production by freshly isolated PBMC. In the latter studies, serial determinations were done only on patients whose PBMC spontaneously produced >1000 pg/ml IgE de novo prior to entry into the study. Of the 14 patients treated with rIFN-γ in part I of the protocol, PBMC from 12 patients produced >1000 pg IgE/ml (mean IgE production=3794 pg/ml; range, 1340–8800). Inhibition of baseline spontaneous de novo IgE synthesis by PBMC was observed between days 1 and 5 at each DL of rIFN-γ treatment. At DL1, spontaneous IgE production was inhibited in 10 of 12 patients. This level of inhibition was significant at a P value of 0.038. At DL2, there was no further inhibition of IgE synthesis noted (P=1.0). At DL3, however, PBMC from 9 to 11 patients studied demonstrated inhibition of spontaneous IgE synthesis following in vivo treatment with rIFN-γ (P=0.066).

Despite the reduction in spontaneous IgE production by PBMC during part I of the protocol, there was no reduction in serum IgE levels noted at any DL (P=0.36). To determine whether any effect could be observed on serum IgE levels with a prolonged course of therapy, 8 additional patients were entered into part II of the protocol which consisted of 6 weeks of daily IFN-γ treatment at DL2 (0.05 mg/$M^2$) which had been well tolerated during part I of the protocol. In addition, a total of 9 patients were followed on long term maintenance therapy after completion of the treatment protocol: one patient from part I received 0.1 mg/$M^2$ rIFN-γ three times per week for 14 months, and all 8 patients from part II received 0.05 mg/$M^2$ rIFN-γ three time per week for between 1 month to 6 months.

Figure 2:
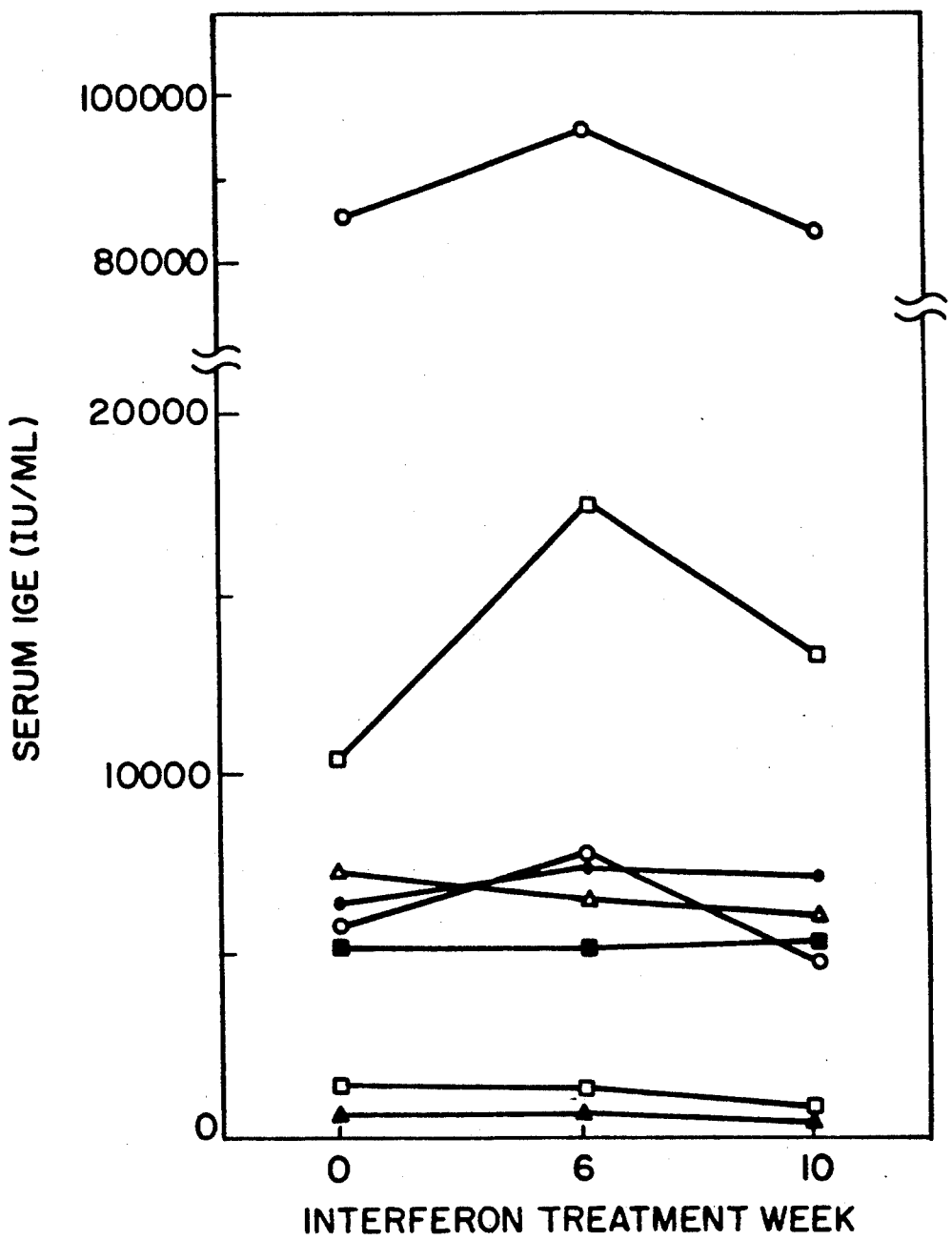
FIG. 2 is a graph showing serum IgE levels of patients with atopic dermatitis on daily IFN-$\gamma$ treatment (0.05 mg/M$^2$) for 6 weeks followed by maintenance IFN-$\gamma$ treatment (3 doses per week of 0.05 mg/M$^2$).

PBMC from six of the eight patients who entered into part II of the protocol spontaneously produced elevated levels of IgE. As shown in FIG. 1, PBMC from 5 of these 6 patients demonstrated reduction of spontaneous IgE production after 6 weeks of rIFN-γ treatment. The degree of inhibition, however, was variable ranging from 12%–85% inhibition and not significant (P=0.12). FIG. 2 shows the serial serum IgE levels while patients were on 6 weeks of daily rIFN-γ treatment. No inhibitory effect was noted on serum IgE levels. Furthermore, no changes in serum IgE levels have been noted in any patients treated for up to 14 months on maintenance rIFN-γ therapy.

Figure 3:
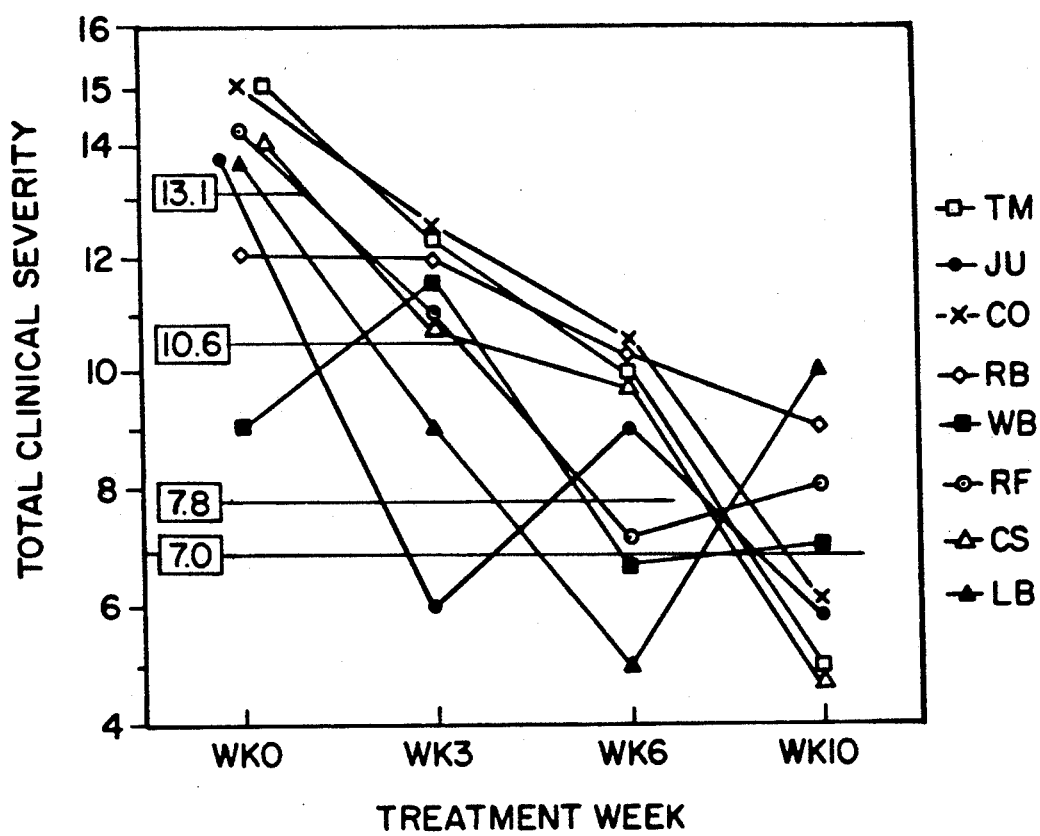
FIG. 3 is a graph showing total clinical severity scores of patients with atopic dermatis on daily IFN-$\gamma$ treatment (0.05 mg/M$^2$) for 6 weeks followed by maintenance IFN-$\gamma$ treatment (3 doses per week of 0.05 mg/M$^2$).

During this trial patients were monitored for changes in the 5 parameters of clinical severity described in the Methods section. Each patient served as his own historical control. There were significant decreases observed in clinical severity for each DL over the 3 week treatment period during part I of the protocol (P<0.04). There was also a nearly significant (P=0.10) worsening of total clinical severity three days after DL3 was discontinued. Furthermore, during part II, there was a progressive and significant reduction in total clinical severity over the 6 weeks of daily rIFN-γ therapy (P<0.01) with a leveling off of clinical improvement after patients were placed on maintenance therapy (FIG. 3). Patients on maintenance therapy have has sustained clinical improvement of their AD compared to clinical symptoms experienced prior to therapy.

Treatment of Steriod-Dependent Asthma

One of the 22 patients treated in Part 1 of the study was afflicted with chronic severe, steroid-dependent asthma in addition to atopic dermatitis. This patient had required treatment with systemic steroids for at least 6 years prior to the study. This patient showed a significant improvement in asthma symptoms and was able to discontinue systemic steroid treatment after treatment with IFN-γ. This patient, in prophylactic or maintenance therapy with IFN-γ, has not required systemic steroids for over one year.

Patients who received daily rIFN-γ therapy experienced a significant reduction in the clinical severity of their skin disease. Since these patients had a history of long standing severe AD poorly responsive to other forms of therapy, it is unlikely that their sustained clinical improvements (while on IFN-γ therapy) was merely due to a placebo effect. Furthermore, patients clinical symptoms worsened (rebound effect) when rIFN-γ therapy was stopped after DL3 of part I of the protocol.

Equivalents

These skilled in the art will recognize or be able to ascertain using no more than routine experimentation, many equivalents to the subject embodiments of the invention described herein. Such equivalents are intended to be encompassed by the following claims.

We claim:

1. A method of treating an individual having Type 1 atopic dermatitis comprising administering to the individual an amount of gamma interferon sufficient to reduce, ameliorate or eliminate clinical symptoms of the Type 1 atopic dermatitis.

2. A method of claim 1 wherein the gamma interferon is recombinant gamma interferon.

3. A method of claim 2 wherein the dosage level of gamma interferon is from about 0.01 mg/$M^2$ to about 0.1 mg/$M^2$ per day.

4. A method of claim 3 wherein the dosage level of gamma interferon is about 0.05 mg/$M^2$ per day.

5. A method of claim 1 wherein the gamma interferon is administered by a method selected from the group consisting of: orally, parenterally, subcutaneously, intravenously, transdermally, by an implanted reservoir and by a drug delivery device.

6. A method of claim 5 wherein the gamma interferon is administered subcutaneously.

7. A method of claim 1 further comprising administering in conjunction with gamma-interferon at least one additional drug, which is effective for reducing, ameliorating or eliminating the symptoms of atopic dermatitis.

8. A method of treating steroid-dependent asthma comprising administering to a human or animal afflicted with steroid-dependent asthma an amount of gamma interferon sufficient to reduce, ameliorate or eliminate clinical symptoms of steroid-dependent asthma.

9. A method of claim 8 wherein the gamma interferon is recombinant gamma interferon.

* * * * *